(12) United States Patent
Homer

(10) Patent No.: US 9,050,116 B2
(45) Date of Patent: Jun. 9, 2015

(54) DERMAL RETRACTION WITH INTERSECTING ELECTROMAGNETIC RADIATION PATHWAYS

(76) Inventor: Gregg S. Homer, Los Angeles, CA (US)

( * ) Notice: Subject to any disclaimer, the term of this patent is extended or adjusted under 35 U.S.C. 154(b) by 2537 days.

(21) Appl. No.: 10/966,794

(22) Filed: Oct. 14, 2004

(65) Prior Publication Data

US 2005/0080466 A1 Apr. 14, 2005

Related U.S. Application Data

(60) Provisional application No. 60/521,750, filed on Jun. 29, 2004, provisional application No. 60/511,251, filed on Oct. 14, 2003.

(51) Int. Cl.
*A61B 19/00* (2006.01)
*A61B 18/20* (2006.01)
*A61N 5/067* (2006.01)
*A61B 18/00* (2006.01)

(52) U.S. Cl.
CPC ..... *A61B 18/203* (2013.01); *A61B 2018/00452* (2013.01); *A61B 2018/0047* (2013.01); *A61B 2018/208* (2013.01)

(58) Field of Classification Search
CPC ...... A61B 18/00; A61B 18/20; A61B 18/201; A61B 18/203; A61B 2018/2005; A61B 2018/2035; A61B 2018/2065; A61B 2018/208; A61B 2018/00315; A61B 2018/0047; A61B 5/441; A61B 5/442; A61N 5/00; A61N 5/06; A61N 5/067

USPC ........... 606/3–13, 16–19; 607/88–91, 93–95, 607/9–11, 13, 17–19; 128/898
See application file for complete search history.

(56) References Cited

U.S. PATENT DOCUMENTS

| | | | |
|---|---|---|---|
| 5,405,368 A | 4/1995 | Eckhouse | |
| 5,425,754 A | 6/1995 | Braun et al. | |
| 5,549,596 A * | 8/1996 | Latina | 606/4 |
| 5,586,981 A * | 12/1996 | Hu | 606/9 |
| 5,669,916 A | 9/1997 | Anderson | |
| 5,720,772 A | 2/1998 | Eckhouse | |
| 5,735,844 A * | 4/1998 | Anderson et al. | 606/9 |
| 5,860,967 A * | 1/1999 | Zavislan et al. | 606/9 |
| 5,961,543 A | 10/1999 | Waldman | |
| 6,162,211 A * | 12/2000 | Tankovich et al. | 606/9 |
| 6,168,590 B1 * | 1/2001 | Neev | 606/9 |
| 6,214,034 B1 | 4/2001 | Azar | |
| 6,228,074 B1 | 5/2001 | Almeida | |
| 6,235,015 B1 * | 5/2001 | Mead et al. | 606/9 |
| 6,251,102 B1 * | 6/2001 | Gruzdev et al. | 606/10 |
| 6,428,532 B1 * | 8/2002 | Doukas et al. | 606/9 |
| 6,447,503 B1 * | 9/2002 | Wynne et al. | 606/9 |
| 6,613,042 B1 * | 9/2003 | Tankovich et al. | 606/10 |
| 6,702,808 B1 | 3/2004 | Kreindel | |
| 6,736,807 B2 * | 5/2004 | Yamazaki et al. | 606/9 |
| 8,852,104 B2 * | 10/2014 | Oralkan et al. | 600/439 |
| 2004/0102799 A1 * | 5/2004 | Perez et al. | 606/166 |

(Continued)

*Primary Examiner* — Ahmed Farah

(57) ABSTRACT

A method and device for stimulating human dermal tissue retraction and collagen and elastin production is provided. One or more lasers or other electromagnetic radiation devices produce at least two output beams (split or independent beams) that can be directed to deliver electromagnetic energy to a desired subsurface depth of dermal tissue, thereby disrupting the same, without causing excessive damage to the adjacent epidermis, subcutaneous fatty tissue, or blood vessels of the skin.

47 Claims, 8 Drawing Sheets

(56) References Cited

U.S. PATENT DOCUMENTS

| | | |
|---|---|---|
| 2005/0273089 A1 | 12/2005 | Kreindel et al. |
| 2007/0179481 A1* | 8/2007 | Frangineas et al. ............... 606/9 |
| 2007/0213791 A1* | 9/2007 | Van Hal et al. .................. 607/89 |
| 2008/0172047 A1* | 7/2008 | Altshuler et al. ................. 606/9 |

* cited by examiner

**Figure 4
Slant Beam Damage Pattern
--NOT DRAWN TO SCALE--**

Direct Damage Pattern
Width: 10,000 μ
Height: 100 μ
Depth: -150 μ to -450 μ
Slope: 3%

Spacing Pattern
(Direct and Residual)
Width: 200 μ
Height: 100 μ
Total (End to End): 223.606 μ

Residual Damage Pattern
Width: 10,100 μ
Height: 200 μ
Depth: -100 μ to -500 μ
Slope: 3%

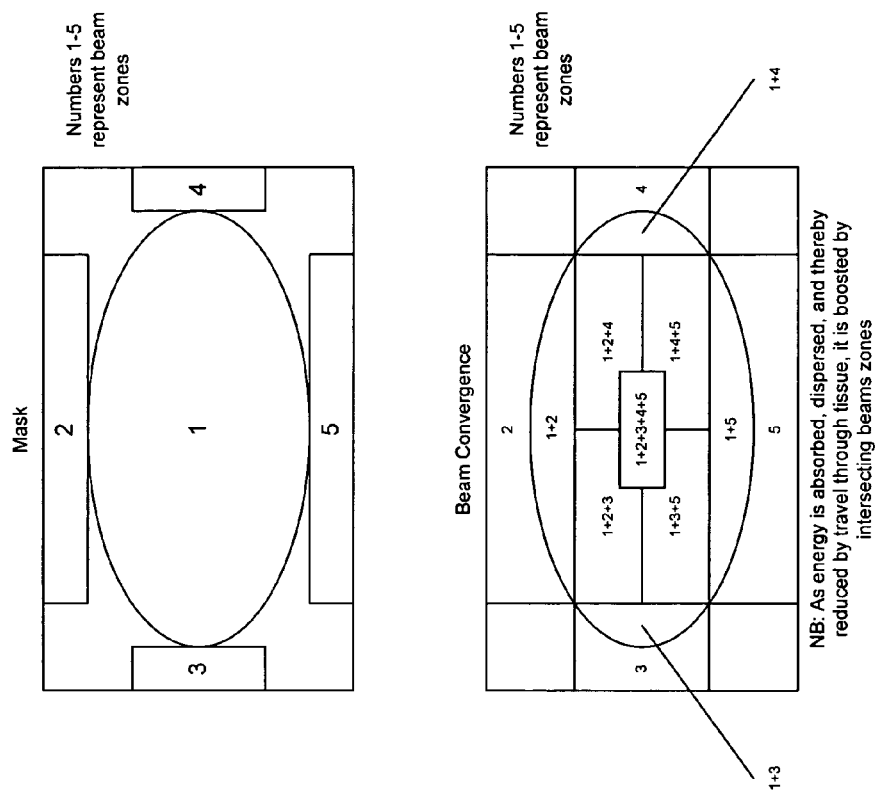
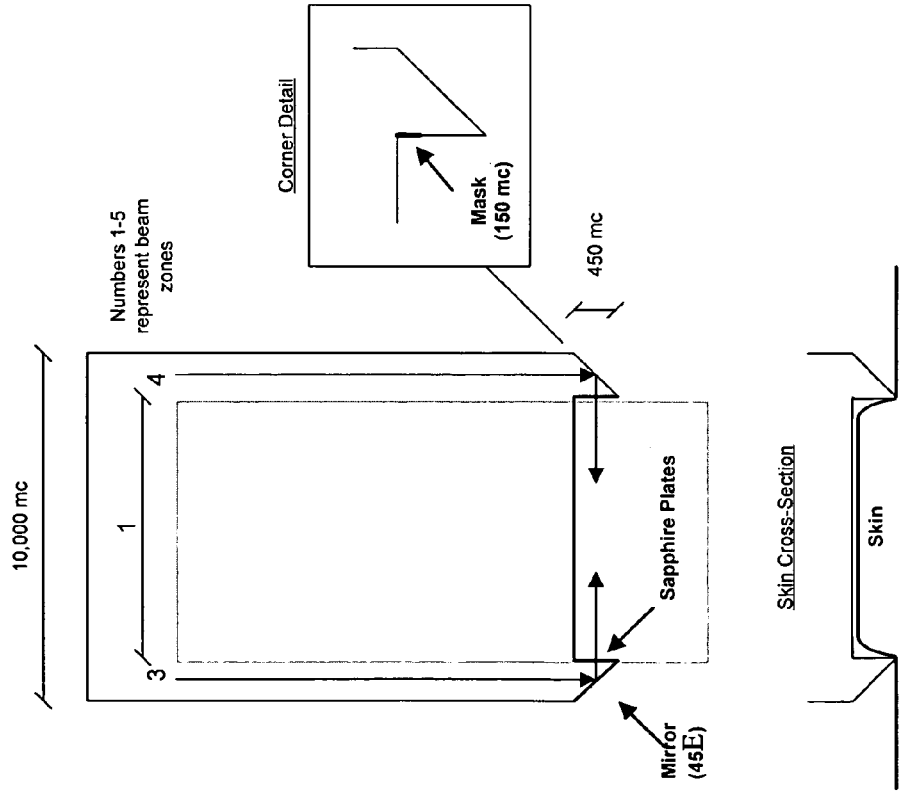
**Figure 6
Surround Beam
--NOT DRAWN TO SCALE--**

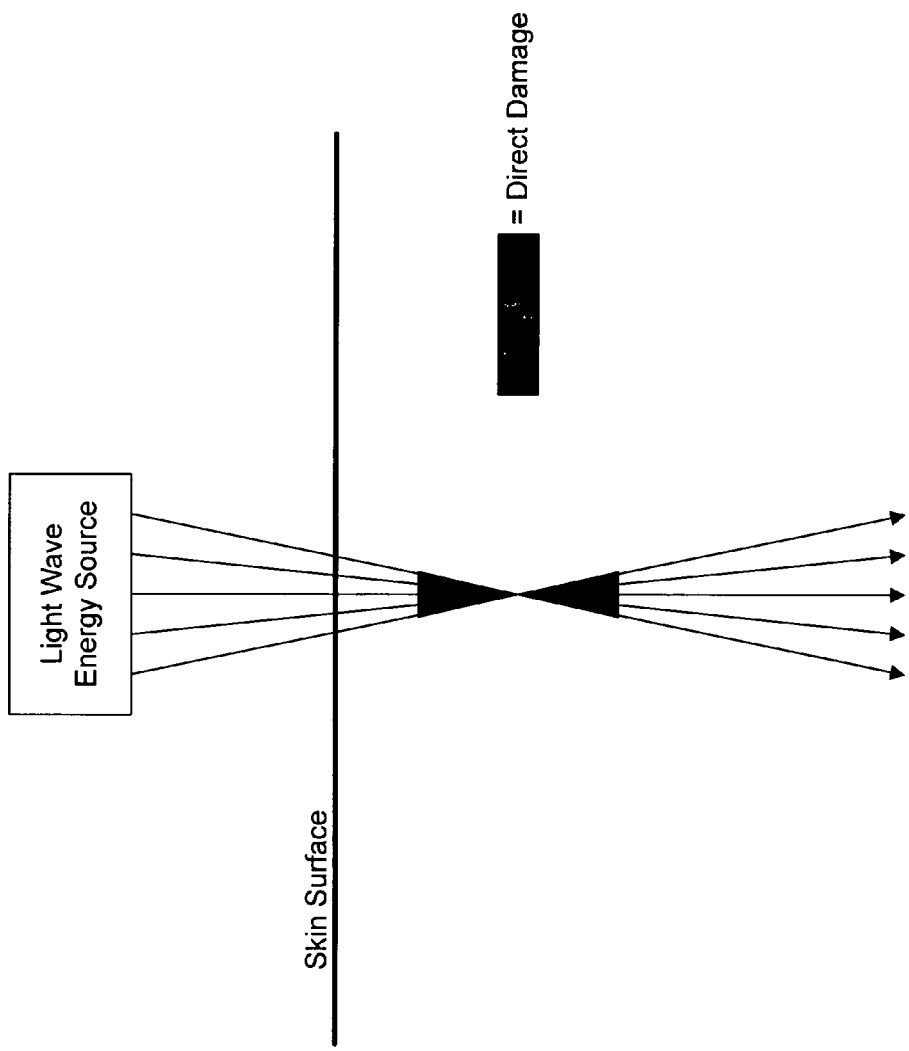

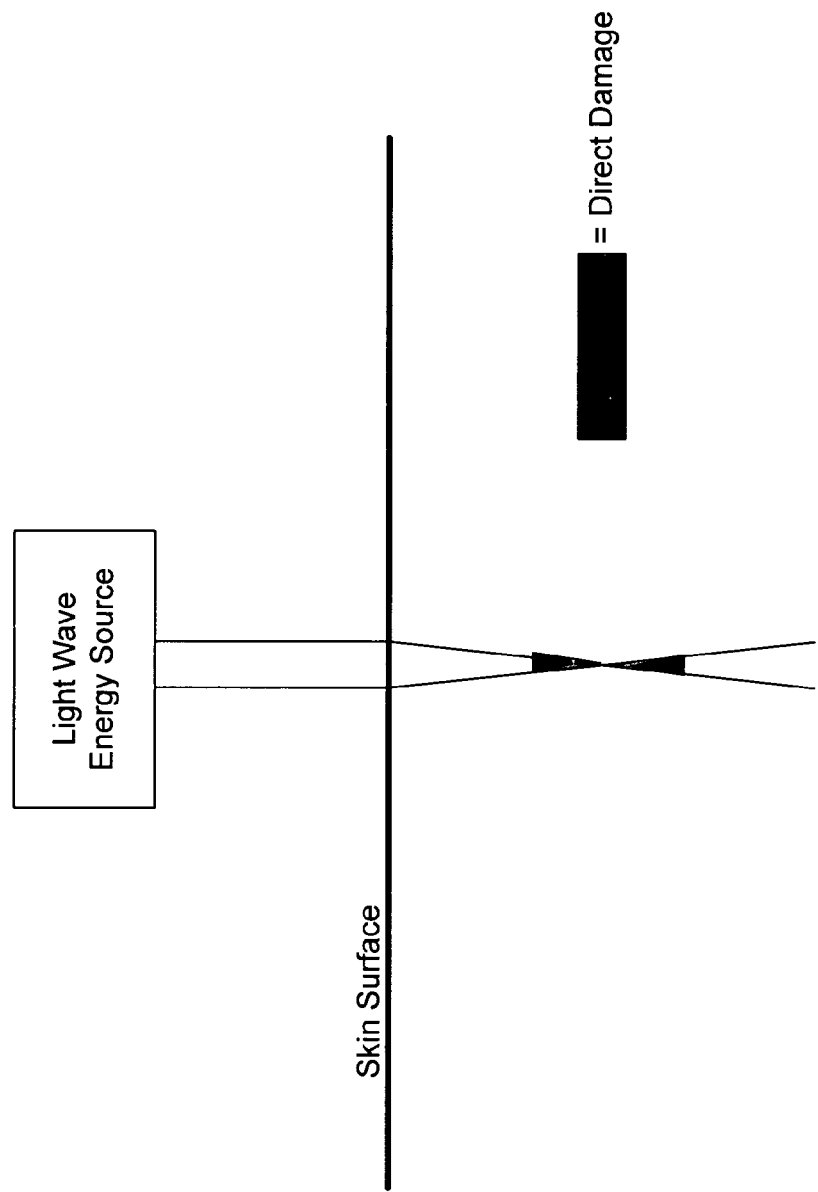

DERMAL RETRACTION WITH INTERSECTING ELECTROMAGNETIC RADIATION PATHWAYS

CROSS-REFERENCES TO RELATED APPLICATIONS

The present application claims the benefit of U.S. provisional patent application No. 60/511,251, filed Oct. 14, 2003, entitled "System for Dermal Retraction and Collagen and Elastin Generation," and U.S. provisional patent application No. 60/521,750, filed Jun. 29, 2004, entitled "System for Dermal Retraction and Collagen and Elastin Generation," which are all incorporated by reference.

BACKGROUND OF THE INVENTION

As humans age, their skin loses elasticity and becomes lax. The combined effects of sunlight (photodamage) and gravity result in the collection of loose skin in the regions of the face (particularly around the eyes, jaw line, chin, and neck) and the body (predominantly the waistline and buttocks). They also cause wrinkling of the skin. Many individuals are concerned with these and other signs of aging and look for ways to slow or reverse them in order to preserve or achieve a youthful appearance.

The current techniques for treating skin laxity of the face include the surgical face lift and the retraction of dermal tissue through the use of electromagnetic radiation (hereinafter "EMR"), i.e., such as laser, radio frequency, or ultrasound. The surgical facelift is a highly invasive procedure that poses many risks of permanent injury, produces several undesirable side effects, and requires a long recovery period. Potential risks of injury include scarring, nerve damage, surgical infection, loss or displacement of subcutaneous fatty tissue, and complications arising from general anesthesia. Side effects include unnatural distributions of elasticity and laxity and thinning of the skin (which, in turn, results in further laxity). And the typical recovery period for a full facelift is roughly two weeks. Recovery can take longer depending upon the age and medical condition of the patient and any complications from surgery. Skin laxity of the body, by contrast, is typically treated by surgically removing excess skin and then closing the skin with sutures the so called "tummy tuck." The risks and side effects are generally the same as those involved in a facelift.

It is known that EMR can cause retraction of dermal tissue. The radiation disrupts the tissue, causing it to produce additional collagen and elastin, which, in turn, results in tightening and retraction of the irradiated dermal tissue. Conventional methods have been proposed using EMR to restore elasticity to aging skin. FIG. 1 illustrates a conventional EMR treatment method, a single EMR device is used to direct a single beam or other energy path (hereinafter, a "beam") into the skin without differentiation as to the energy applied at any given depth of penetration. The resulting damage pattern from this treatment is shown in FIG. 1. This method, as well as other conventional methods, have encountered a fundamental problem: in order to deliver sufficient level of energy to the dermal tissue to produce the desired effect, they cause excessive damage to the superficial adjacent epidermis and the deeper adjacent subcutaneous fatty tissue, as well as the blood vessels of the skin.

Some injury to these structures may be inevitable using EMR treatment methods. But a medically acceptable method of delivering EMR to the dermis should achieve a level of disruption to the dermal layer sufficient to create significant retraction of the dermal tissue while avoiding excessive damage to these adjacent structures.

BRIEF SUMMARY OF THE INVENTION

The present invention achieves a level of disruption to the dermal layer sufficient to create significant retraction of the dermal tissue while avoiding excessive damage to these adjacent structures. By focusing EMR at the depth of the dermis, the present invention avoids excessive damage to the epidermis, the subcutaneous fatty tissue, and the blood vessels of the skin. In a preferred embodiment of the present invention, one laser or other EMR device is used. The output beam of this device is split into two or more output beams of lesser fluence (i.e., energy per unit area). By using mirrors, prisms, or other devices (hereinafter, "reflective devices") capable of altering the path of these output beams, these beams are then redirected to a point of intersection located at the desired dermal depth. The energy produced by each split beam alone is insufficient to create either the desired level of disruption to the dermis or an excessive degree of damage to the epidermis, the subcutaneous fatty tissue, or the blood vessels of the skin. At the point of intersection of these beams, however, the cumulative energy that is generated is sufficient to cause the desired level of dermal tissue disruption and produce dermal retraction at the desired dermal depth.

In another embodiment of the present invention, one or more laser or other EMR devices are used that produce more than one output beam. These beams are directed to a point of intersection located at the desired dermal depth. The energy produced by each beam alone is insufficient to create either the desired level of disruption to the dermis or an excessive degree of damage to the epidermis, the subcutaneous fatty tissue, or the blood vessels of the skin. At the point of intersection of these beams, however, the cumulative energy that is generated is sufficient to cause the desired level of dermal tissue disruption and produce dermal retraction at the desired dermal depth.

In yet another embodiment of the present invention, a method of treating skin is provided. A first beam is directed to a skin surface at a first angle. A second beam is directed to the skin surface at a second angle. The first beam and the second beam traverse in a treatment area underlying the skin surface, whereby an cumulative energy level in the treatment area from the first beam and the second beam is within a predetermined range.

According to another embodiment of the present invention, a skin treatment apparatus is provided. The skin treatment apparatus includes at least one electromagnetic radiation device capable of providing at least two beams. At least one reflective device directs the at least two beams towards a skin surface at differing angles. The cumulative energy of the at least two beams is sufficient to cause dermal tissue disruption, but the individual energy of each of the at least two beams alone is insufficient to cause dermal tissue disruption.

Various additional objects, features, and advantages of the present invention can be more fully appreciated with reference to the detailed description and accompanying drawings that follow.

BRIEF DESCRIPTION OF THE DRAWINGS

These and other features, aspects, and advantages of the present invention will become better understood with reference to the following drawings, description, and appended claims, where:

FIG. 4 shows an exemplary set of dimensions for the embodiments represented in FIGS. 2-3.

FIG. 6 illustrates a simplified diagram of an embodiment of the present invention.

FIG. 7 illustrates a simplified diagram of an embodiment of the present invention.

FIG. 8 illustrates a simplified diagram of an embodiment of the present invention.

DETAILED DESCRIPTION OF THE INVENTION

Figure 1:
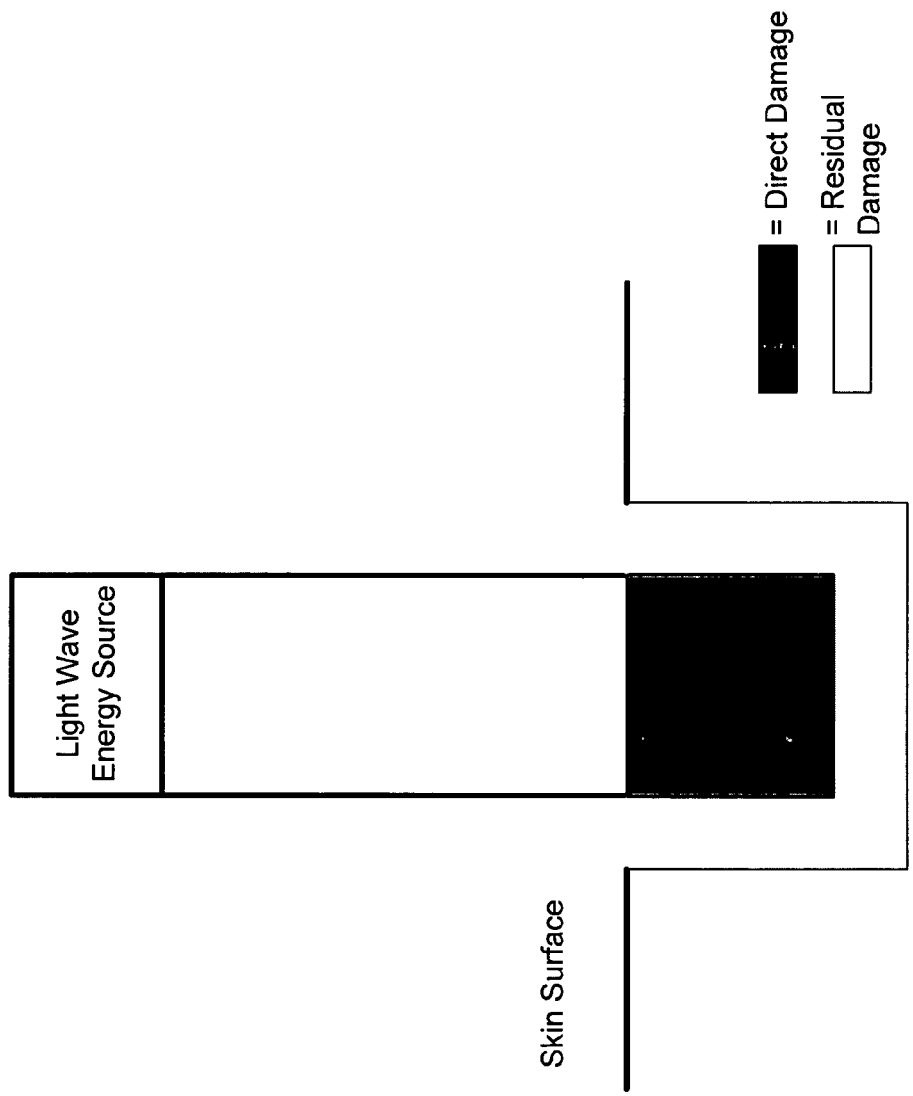
FIG. 1 illustrates a conventional EMR treatment method and resulting damage pattern.

In a preferred embodiment of the present invention, one laser or other EMR device is used. The output beam of this device is split into two or more output beams of lesser fluence. By using mirrors or other reflective devices, these beams are then redirected to a point of intersection located at the desired dermal depth. The energy produced by each split beam alone is insufficient to create either the desired level of disruption to the dermis or an excessive degree of damage to the epidermis, the subcutaneous fatty tissue, or the blood vessels of the skin. At the point of intersection of these beams, however, the cumulative energy that is generated is sufficient to cause the desired level of dermal tissue disruption and produce dermal retraction at the desired dermal depth.

In another preferred embodiment of the present invention, one or more laser or other EMR devices are used that produce more than one output beams. These beams are directed to a point of intersection located at the desired dermal depth. The energy produced by each beam alone is insufficient to create either the desired level of disruption to the dermis or an excessive degree of damage to the epidermis, the subcutaneous fatty tissue, or the blood vessels of the skin. At the point of intersection of these beams, however, the cumulative energy that is generated is sufficient to cause the desired level of dermal tissue disruption and produce dermal retraction at the desired dermal depth.

In another embodiment, the present invention comprises a method of treating skin, the method comprising: directing a first beam to a skin surface at a first angle; directing a second beam to the skin surface at a second angle, wherein the first beam and the second beam intersect in a treatment area underlying the skin surface, and a cumulative energy level in the treatment area of the first beam and the second beam is within a predetermined range. In other embodiments: the foregoing first angle is about perpendicular to the skin surface; the foregoing second angle is within a range of about parallel to skin surface (0 degrees) to about perpendicular to skin surface (90 degrees); and/or the foregoing first beam and the foregoing second beam each has a spot size within a range of about 5 microns to about 3 inches in diameter.

In another embodiment, the present invention comprises a skin treatment apparatus comprising: at least one electromagnetic radiation device providing at least two beams; at least one reflective device to direct the at least two beams towards a skin surface at differing angles, wherein a cumulative energy of the at least two beams is sufficient to cause dermal tissue disruption, and an energy level of each of the at least two beams is insufficient to cause dermal tissue disruption. In another embodiment, one beam of the foregoing at least two beams is pulsed, and the one beam has a pulse rate period ranging from about 1 femtosecond to about 1 second.

Because most EMR devices are capable of tissue penetration and damage, and because the present invention employs a convergence of multiple beams to generate energy at the desired depth of focus or convergence, the specific medium and wavelength of the EMR device is not critical. The present invention is suited to a broad range of sound, heat, and light generating devices, including radio frequency, ultrasound, microwave, and laser. Suitable laser media include gas (e.g., Helium Neon, Helium Cadmium, Copper Vapor, Gold Vapor, Carbon Dioxide, Nitrogen, Chemical (HF DF), Far Infrared, Excimer, Argon Ion, and Krypton Ion), liquid (e.g., dye), and solid state (e.g., Ruby, Nd: YAG, Nd: Glass, Erbium: YAG, Color Center, Alexandrite, Ti Sapphire, and Semiconductor Diode), as well as x ray and free electron varieties. In a preferred embodiment of the present invention, the EMR device consists of a solid state tunable laser, with a wavelength of 1064 nanometers. In another preferred embodiment of the present invention, the EMR device is an erbium: YAG laser, with a wavelength greater than 2000 nanometers.

The term "electromagnetic radiation" or "EMR" is intended to include any and all forms of wave energy or oscillations propagating energy through a medium or space, whether in the form of sound, heat, light, electricity, magnetism, or otherwise. Without limiting the foregoing, EMR includes any and all forms of electromagnetic radiation, such as radio frequency, microwave, ultrasound, infrared, visible light, ultraviolet light, x ray, t ray (terahertz radiation), and gamma ray. EMR may or may not be monochromatic (i.e., it may be composed of one or more than one different wavelengths), directional (i.e., it may produce a single non divergent spot or it may radiate in several different directions), or coherent (i.e., the waves produced may consist of a single phase relation or of multiple phase relations). In addition, EMR may be delivered through any medium, including gas, liquid, or solid matter. It may also be delivered in pulses or continuously, and if pulsed, each pulse may consist of a buildup of concentrated energy or a series of unconcentrated exposures. Pulsed outputs may also occur at any rate of speed, including milliseconds, microseconds, nanoseconds, or femtoseconds.

Spot size, too, may vary, depending upon the width and depth of the target area and the sensitivity of the adjacent tissue. The larger the spot, the wider, deeper, and less precise the area of energy concentration; the smaller the spot, the longer the treatment time. In some of the preferred embodiments contemplated by this application, at least two beams would be used, and the spot size of one beam will typically be larger than the spot size of the other beam. In the preferred embodiments represented in FIGS. 2-5, the spot of the vertical beam might be in the shape of an ellipse with x=10,000 microns and y=5,000 microns, and the spot of the transverse beam might be in the shape of a rectangle with x=100 microns and y=5,000 microns, thereby producing a direct damage pattern at the point of intersection in the shape of a right elliptical cylinder section with surface coordinates x=5,000 microns and y=10,000 microns, and depth coordinate z=100 microns, tilted at a slope of 3 percent. Preferred embodiments also include more than two beams and/or alternative spot shapes, sizes, and combinations. In other preferred embodiments contemplated by this application, at least two beams would be used, and the spot size of each beam would be similar.

The lasers required for the foregoing preferred embodiments are readily commercially available. Cynosure, Inc. (Chelmsford, Mass., USA), for example, manufactures the TriStar Aesthetic Workstation, a combination pulsed dye and Nd:YAG laser. The Nd:YAG option produces wavelengths of 1064 nanometers and 1320 nanometers and fluences of 35 J/cm.sup.2 and 20 J/cm.sup.2, respectively, at a spot size of 10 millimeters. Adept Medical Concepts, Inc. (Rancho Santa Margarita, Calif., USA) offers the UltraWave II, a combination Alexandrite and Nd:YAG laser, with wavelengths of 755 and 1064 nanometers, a tunable energy output of 5 to 500 J/cm.sup.2, a tunable pulse length of 5 to 100 ms, and an adjustable spot size ranging from 2 to 12 millimeters at 1064 nanometers. Alpes Lasers SA (Neuchtel, Switzerland) produces a line of tunable infrared diode lasers that operate at or near room temperature in a variety of tunable infrared wavelengths, tunable energy outputs, tunable pulse lengths, and adjustable spot sizes.

Because the thickness of the epidermal and dermal layers of the skin varies from individual to individual, age to age, and treatment area to treatment area, the target focal point of beam convergence will vary as well. Epidermal thickness ranges from 50 to 100 microns, and dermal thickness ranges from 300 to 2,000 microns. The thinner dermal tissue generally appears around the eyes, and the thicker dermal tissue typically appears on the back and buttock. The center of the target depth will typically be located at the center of the dermal layer of the skin, but shallower and deeper target depths are possible, depending upon such variables as skin thickness, body area, treatment response, spot size and position, EMR medium, fluence and frequency, and skin anatomy. In the preferred embodiments represented in FIGS. 2-8, the skin of the cheeks of the face are treated, and the target depth is from −150 to −450 microns below the surface of the skin (with an expected residual damage pattern of −100 to −500 microns below the skin surface). The EMR device is moved across the surface of the treatment area until the entire has been treated in the manner herein described.

Preferred embodiments will probably spare some of the dermal tissue between each direct and/or residual damage zone in order to aid in the collagen generation and tissue retraction processes. The spared tissue areas might range from 10 to 10,000 microns, depending upon such variables as skin thickness, body area, treatment response, spot size and position, EMR medium, fluence and frequency, and skin anatomy. It is possible that no tissue between damage zones will be spared. In the preferred embodiments represented in FIGS. 2-8, the residual damage areas are spaced 150 to 250 microns apart.

Figure 2:
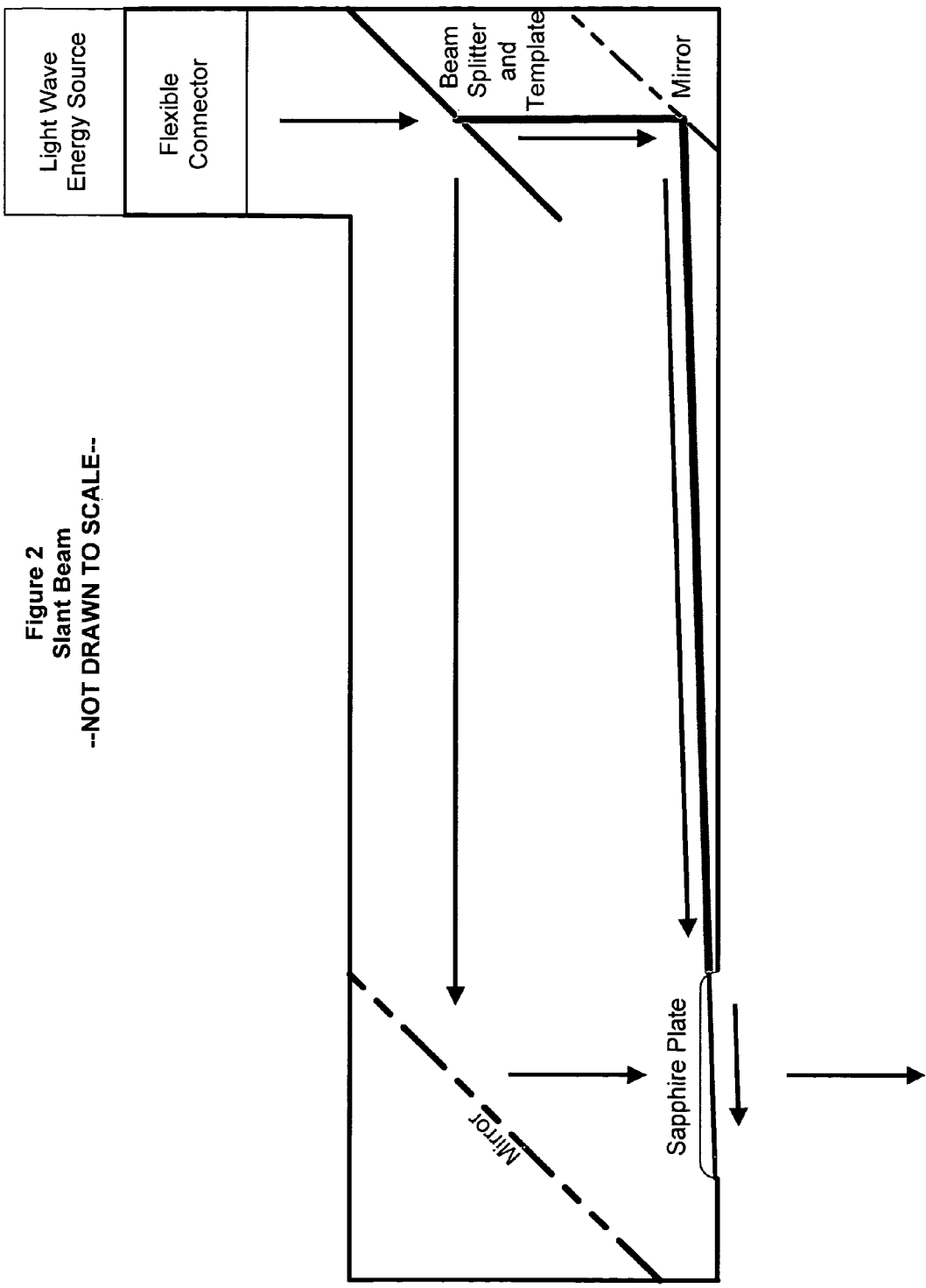
FIGS. 2-3 show simplified diagrams of exemplary embodiments of the present invention, whereby one laser or other EMR device produces one beam, and that beam is then split into at least two beams, which beams are redirected with reflective devices to converge upon a predetermined depth of penetration within the dermis.
Figure 3:
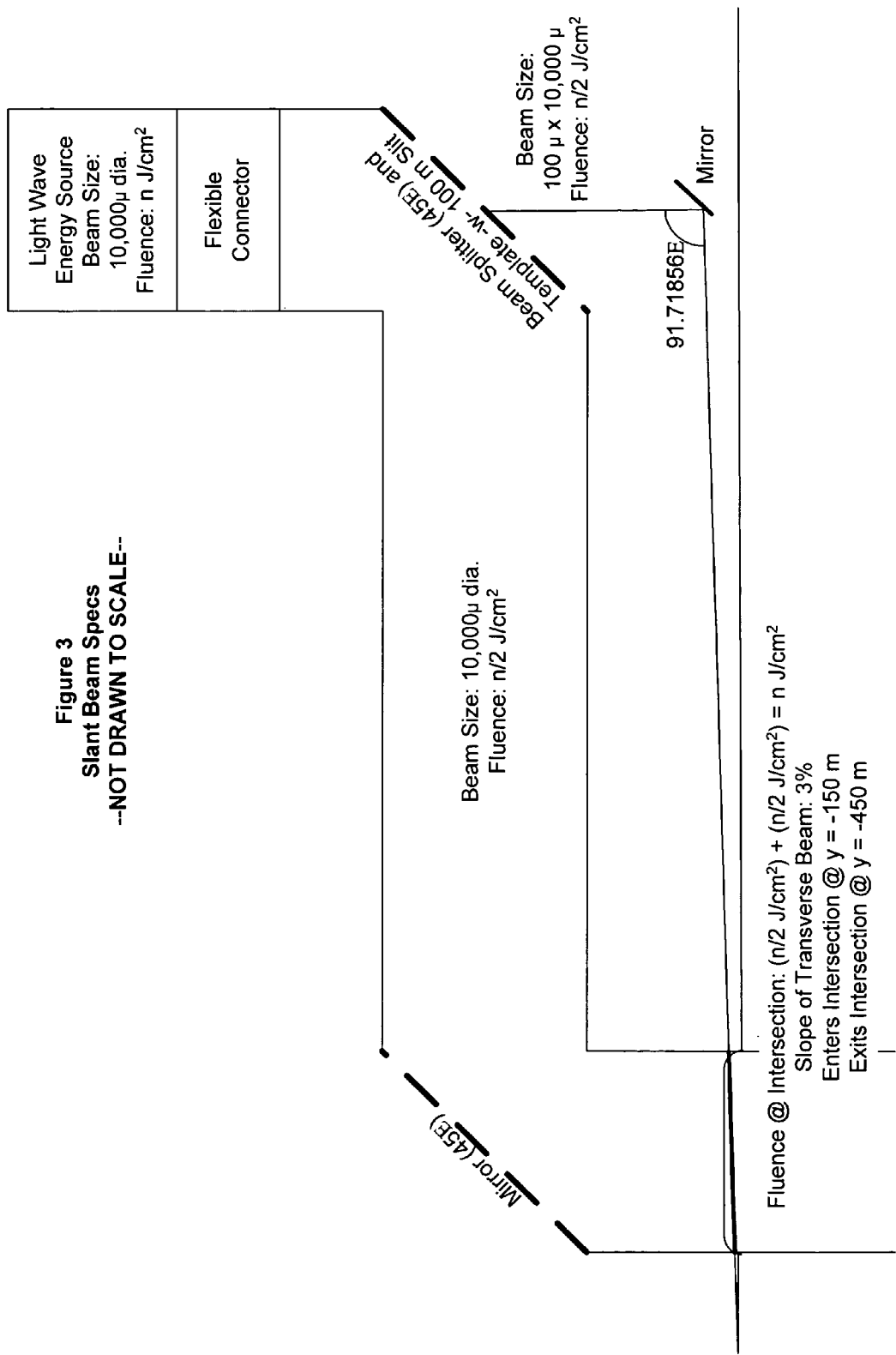

FIGS. 2-3 illustrate a simplified diagram of an embodiment of the present invention. One or more lasers produce more than one beam, and those beams converge both parallel to and at an acute angle to the skin at a predetermined depth of penetration within the dermis.

FIG. 4 illustrates a simplified diagram of the damage pattern expected to result from the application of the embodiment illustrated in FIGS. 2-3.

Figure 5:
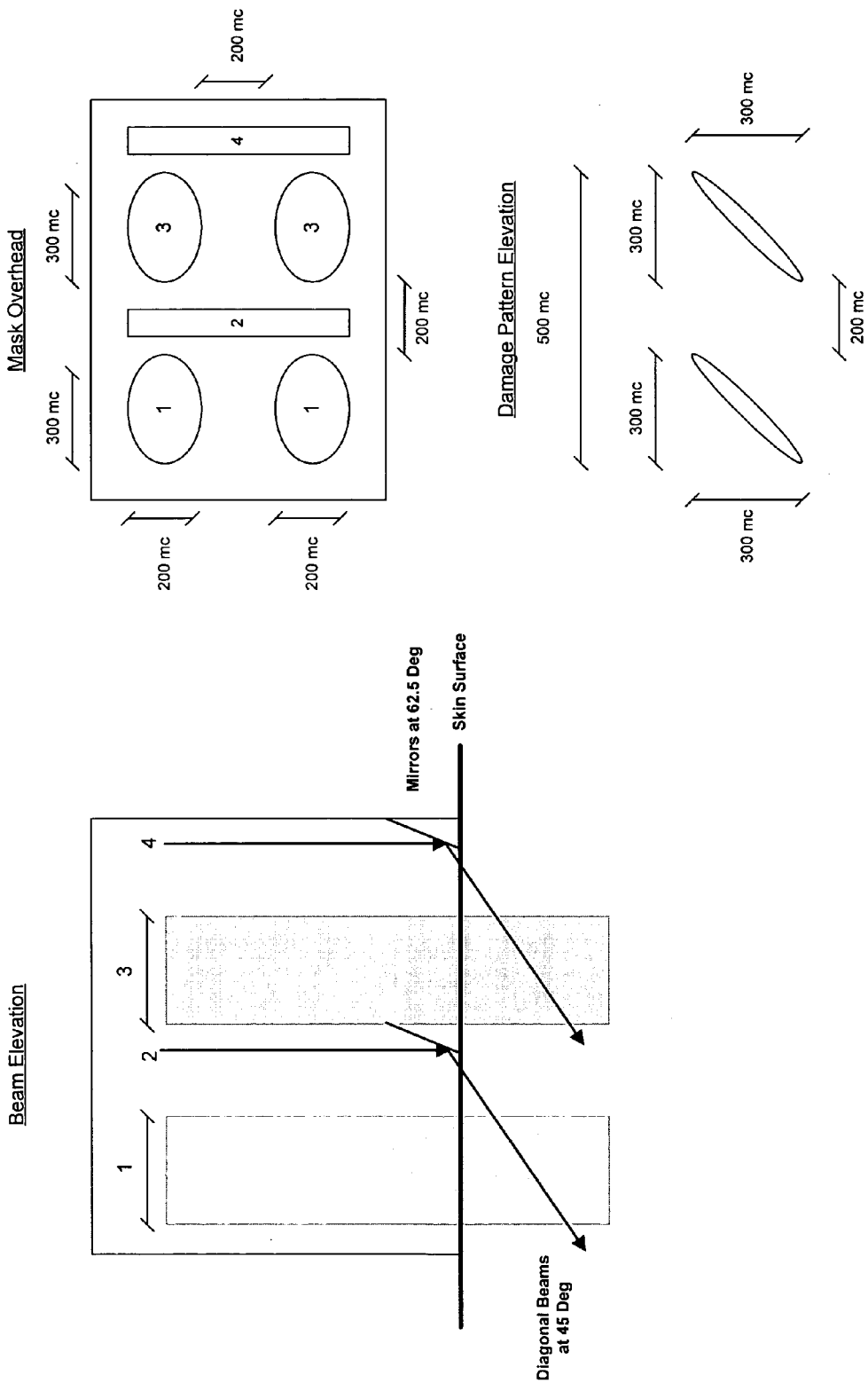
FIG. 5 illustrates expected damage patterns produced according to embodiments of the present invention.

FIG. 5 illustrates a simplified diagram of an embodiment of the present invention. One or more lasers produce more than one beam, and those beams converge at multiple points both parallel to and at an acute angle to the skin at a predetermined depth of penetration within the dermis.

FIG. 6 illustrates a simplified diagram of an embodiment of the present invention. One or more lasers produce more than one beam, and those beams converge both perpendicular and parallel to the skin at a predetermined depth of penetration within the dermis.

FIG. 7 illustrates a simplified diagram of an embodiment of the present invention. One or more lasers produce an array consisting of two or more beams, and those beams converge upon a predetermined depth of penetration within the dermis.

FIG. 8 illustrates a simplified diagram of an embodiment of the present invention. An ultra fast pulsed laser produces one beam. The one beam focuses its energy at a predetermined depth of penetration within the dermis.

The target area to be treated may be scanned prior to or during treatment to determine the appropriate depth of subsurface penetration (z) at each surface coordinate (x y). Independently, a computerized guidance system may be used to direct the EMR device across the x y surface coordinates, adjusting the focal depth to accommodate variations in skin thickness at each surface coordinate, until the entirety of the target area is treated. The scanning and guidance systems referenced herein are familiar to those skilled in the art.

In a specific embodiment, the scanning and guidance systems can be implemented by one or more computer systems. An exemplary computer system can include software, monitor, cabinet, keyboard, and mouse. The cabinet can house familiar computer components, such as a processor, memory, mass storage devices, and the like. Mass storage devices may include mass disk drives, floppy disks, Iomega ZIP™ disks, magnetic disks, fixed disks, hard disks, CD-ROMs, recordable CDs, DVDs, DVD-R, DVD-RW, Flash and other non-volatile solid-state storage, tape storage, reader, and other similar media, and combinations of these. A binary, machine-executable version, of the software of the present invention may be stored or reside on mass storage devices. Furthermore, the source code of the software of the present invention may also be stored or reside on mass storage devices (e.g., magnetic disk, tape, or CD-ROM). Furthermore, a computer system can include subsystems such as central processor, system memory, input/output (I/O) controller, display adapter, serial or universal serial bus (USB) port, network interface, and speaker. The present invention may also be used with computer systems with additional or fewer subsystems. For example, a computer system could include more than one processor (i.e., a multiprocessor system) or a system may include a cache memory.

The energy output utilized in this embodiment is determined by the number of beams deployed, the desired depth of focus, the size of the spot, and the wavelength of the EMR device selected. This embodiment could also employ pulsed or continuous output EMR devices, although pulsed devices might be preferred in order to control more precisely any excessive heat or other energy transfer to adjacent tissues. Numerous devices satisfying the foregoing criteria are presently commercially available and are known to those skilled in the art.

The present invention has one or more the following features:
  (a) one laser or other EMR device capable of producing one beam that can then be split into two or more beams of lesser fluence and then redirected, by means one or more reflective devices, to a point of intersection located at the desired subsurface dermal depth, thereby producing a cumulative energy at the point of intersection sufficient to cause the desired level of dermal tissue disruption, but producing insufficient energy to cause excessive damage to the epidermis, the subcutaneous fatty tissue, or the blood vessels of the skin;
  (b) one or more laser or other EMR devices capable of producing two or more beams that can then be directed to a point of intersection located at the desired subsurface dermal depth, thereby producing a cumulative energy at the point of intersection sufficient to cause the desired level of dermal tissue disruption, but producing insufficient energy to cause excessive damage to the epidermis, the subcutaneous fatty tissue, or the blood vessels of the skin;

(c) a scanning device is used to identify the depth of the epidermis, dermis, subcutaneous fatty tissue, and blood vessels of the skin of the subject's face or body;

(d) a data storage device used to store the location of the epidermis, dermis, subcutaneous fatty tissue, and blood vessels of the skin of the subject's face or body gathered by a scanning device;

(e) one or more laser or other EMR devices capable of producing two or more split or independent output beams can be moved over or above the surface of the skin to be treated;

(f) one or more laser or other EMR devices capable of producing two or more split or independent output beams are moved over or above the surface of the skin to be treated with the assistance of a computerized guidance mechanism;

(g) one or more laser or other EMR devices capable of producing two or more split or independent pulsed output beams;

(h) one or more laser or other EMR devices capable of producing two or more split or independent continuous output beams and (i) one or more laser or other EMR devices capable of producing two or more split or independent output beams, one or more of which are pulsed and the remainder of which are continuous.

One of ordinary skill in the art would recognize many other variations, modifications, and alternatives. The above examples are merely illustrations, which should not unduly limit the scope of the claims herein. It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method for retracting dermal tissue located within a predetermined area of skin, the method comprising:
    directing at least two beams of electromagnetic radiation to a skin surface,
    wherein each of the at least two beams is directed to the skin surface at a predetermined angle,
    the at least two beams intersect within a region comprising at least a portion of the dermal tissue,
    energy density of no one beam alone is sufficient to effect a desired retraction of the dermal tissue,
    cumulative energy density generated at the region of intersection is sufficient to effect the desired retraction of the dermal tissue at the region of intersection, and
    the region of intersection is moved about the predetermined area of the skin.

2. The method of claim 1 wherein the cumulative energy density generated at the region of intersection is approximately 5 joules per square centimeter to approximately 500 joules per square centimeter.

3. The method of claim 1 wherein the predetermined angle of at least one beam is within a range from approximately parallel to the skin surface (0 degrees) to approximately perpendicular to the skin surface (90 degrees).

4. The method of claim 1, further comprising positioning at least one of a mirror, prism, or other device capable of altering a path of at least one of the at least two beams.

5. The method of claim 1 wherein at least one of the at least two beams comprises laser radiation.

6. The method of claim 1 wherein wavelength of each of the at least two beams is the same.

7. The method of claim 1 further comprising determining a dermal depth of the treatment area.

8. The method of claim 1 further comprising an electronic guidance system configured to move the region of intersection about the predetermined area of the skin.

9. The method of claim 8 wherein at least two regions of intersection are separated by a region of untreated tissue.

10. The method of claim 1 wherein at least one of the at least two beams has a spot size within a range from approximately 5 microns to approximately 3 inches (i.e., 76,200 microns) in diameter.

11. The method of claim 1 wherein the predetermined area of the skin comprises at least a portion of at least one of an eye, jaw line, chin, neck, forehead, face, hand, waistline, breast, foot, leg, or buttocks.

12. The method of claim 1 wherein wavelengths of at least two of the at least two beams are different.

13. The method of claim 1 wherein the region of intersection does not comprise diseased dermal tissue.

14. The method of claim 1 wherein at least two of the at least two beams are generated by separate electromagnetic radiation devices.

15. The method of claim 1 wherein at least one of the at least two beams comprises radiofrequency radiation.

16. The method of claim 1 wherein at least one of the at least two beams comprises ultrasound radiation.

17. The method of claim 1 wherein at least one of the at least two beams comprises a pulsed wave.

18. The method of claim 17 wherein duration of the pulsed wave is within a range of approximately 1 femtosecond to approximately 1 second.

19. The method of claim 1 wherein at least one of the at least two beams comprises a continuous wave.

20. The method of claim 1 wherein a single electromagnetic device generates each of the at least two beams.

21. The method of claim 1 wherein the at least two beams constitute two beams.

22. The method of claim 1 wherein the at least two beams constitute three beams.

23. A method for retracting dermal tissue located within a predetermined area of skin, the method comprising:
    providing an electromagnetic radiation device configured to direct at least two beams of electromagnetic radiation to a skin surface,
    wherein each of the at least two beams is directed to the skin surface at a predetermined angle,
    the at least two beams intersect within a region comprising at least a portion of the dermal tissue,
    energy density of no one beam alone is sufficient to effect a desired retraction of the dermal tissue,
    cumulative energy density generated at the region of intersection is sufficient to effect the desired retraction of the dermal tissue at the region of intersection, and
    the region of intersection is moved about the predetermined area of the skin.

24. The method of claim 23 wherein the cumulative energy density generated at the region of intersection is approximately 5 joules per square centimeter to approximately 500 joules per square centimeter.

25. The method of claim 23 wherein the predetermined angle of at least one beam is within a range from approximately parallel to the skin surface (0 degrees) to approximately perpendicular to the skin surface (90 degrees).

26. The method of claim 23, further comprising positioning at least one of a mirror, prism, or other device capable of altering a path of at least one of the at least two beams.

27. The method of claim 23 wherein at least one of the at least two beams comprises laser radiation.

28. The method of claim 23 wherein wavelength of each of the at least two beams is the same.

29. The method of claim 23 further comprising determining a dermal depth of the treatment area.

30. The method of claim 23 further comprising an electronic guidance system configured to move the region of intersection about the predetermined area of the skin.

31. The method of claim 30 wherein at least two regions of intersection are separated by a region of untreated tissue.

32. The method of claim 23 wherein at least one of the at least two beams has a spot size within a range from approximately 5 microns to approximately 3 inches (i.e., 76,200 microns) in diameter.

33. The method of claim 23 wherein the predetermined area of the skin comprises at least a portion of at least one of an eye, jaw line, chin, neck, forehead, face, hand, waistline, breast, foot, leg, or buttocks.

34. The method of claim 23 wherein wavelengths of at least two of the at least two beams are different.

35. The method of claim 23 wherein the region of intersection does not comprise diseased dermal tissue.

36. The method of claim 23 wherein at least two of the at least two beams are generated by separate electromagnetic radiation devices.

37. The method of claim 23 wherein at least one of the at least two beams comprises radiofrequency radiation.

38. The method of claim 23 wherein at least one of the at least two beams comprises ultrasound radiation.

39. The method of claim 23 wherein at least one of the at least two beams comprises a pulsed wave.

40. The method of claim 39 wherein duration of the pulsed wave is within a range of approximately 1 femtosecond to approximately 1 second.

41. The method of claim 23 wherein at least one of the at least two beams comprises a continuous wave.

42. The method of claim 23 wherein a single electromagnetic device generates each of the at least two beams.

43. The method of claim 23 wherein the at least two beams constitute two beams.

44. The method of claim 23 wherein the at least two beams constitute three beams.

45. A system for retracting dermal tissue located within a predetermined area of skin, the system comprising:
an electromagnetic radiation device configured to direct at least two beams of electromagnetic radiation to a skin surface,
wherein each of the at least two beams is directed to the skin surface at a predetermined angle,
the at least two beams intersect within a region comprising at least a portion of the dermal tissue,
energy density of no one beam alone is sufficient to effect a desired refraction of the dermal tissue,
cumulative energy density generated at the region of intersection is sufficient to effect the desired retraction of the dermal tissue at the region of intersection, and
the region of intersection is moved about the predetermined area of the skin.

46. The system of claim 45 wherein the at least two beams constitute two beams.

47. The system of claim 45 wherein the at least two beams constitute three beams.

* * * * *